(12) United States Patent
Lane et al.

(10) Patent No.: US 6,545,486 B2
(45) Date of Patent: Apr. 8, 2003

(54) SOLUTION AND METHODOLOGY FOR DETECTING SURFACE DAMAGE ON CAPACITIVE SENSOR INTEGRATED CIRCUIT

(75) Inventors: Fred P. Lane, Highland Village, TX (US); Hoyoung Chang, Flower Mound, TX (US)

(73) Assignee: STMicroelectronics, Inc., Carrollton, TX (US)

( * ) Notice: Subject to any disclaimer, the term of this patent is extended or adjusted under 35 U.S.C. 154(b) by 0 days.

(21) Appl. No.: 09/943,597

(22) Filed: Aug. 30, 2001

(65) Prior Publication Data

US 2003/0042911 A1 Mar. 6, 2003

(51) Int. Cl.$^7$ .................. H01H 31/02; G01R 31/12
(52) U.S. Cl. .................................. 324/537; 324/548
(58) Field of Search .................. 324/514, 548, 324/663, 649, 658, 501, 702, 750, 751, 752, 753, 549; 382/141, 144, 149, 100, 145, 124; 438/250

(56) References Cited

U.S. PATENT DOCUMENTS

| 5,907,627 | A | * | 5/1999 | Borza | 382/124 |
| 5,907,628 | A | * | 5/1999 | Yolles et al. | 382/149 |
| 6,437,583 | B1 | * | 8/2002 | Tartagni et al. | 324/687 |

* cited by examiner

Primary Examiner—N. Le
Assistant Examiner—Donald M Lair
(74) Attorney, Agent, or Firm—Lisa K. Jorgenson; William A. Munck

(57) ABSTRACT

Minute surface damage or irregularities on the sensing surface of a capacitive sensor integrated circuit is detected by acquiring a preliminary image of the capacitance readings for the sensor array, coating the sensing surface with an electrolyte solution, then acquiring an additional image while the sensing surface is coated and/or after the electrolyte solution is removed. The electrolyte solution accelerates manifestation of pixel degradation or failure caused by surface damage or irregularities. Defective regions are identified by change of grayscale pixels in the preliminary image while the electrolyte coating is on the sensing surface and then again after the electrolyte coating is removed.

20 Claims, 3 Drawing Sheets

SOLUTION AND METHODOLOGY FOR DETECTING SURFACE DAMAGE ON CAPACITIVE SENSOR INTEGRATED CIRCUIT

TECHNICAL FIELD OF THE INVENTION

The present invention is directed, in general, to detecting defects in integrated circuits and, more specifically, to detecting surface damage or other irregularities at minute levels on the surface of capacitive sensor integrated circuits.

BACKGROUND OF THE INVENTION

Unlike typical integrated circuits which are completely encapsulated in protective packaging except for conductive leads or pins, fingerprint sensors and other capacitive integrated circuits must necessarily include an exposed sensor surface proximate to the integrated circuit core. A simplistic example is illustrated in FIGS. 3A and 3B. FIG. 3A is a plan view of a capacitive fingerprint sensor 300 showing the layout of capacitive sensor electrodes without overlying dielectric or passivation layers; FIG. 3B is a cross-sectional view of the capacitive fingerprint sensor 300 taken at section line A—A, showing the overlying layers.

Capacitive fingerprint sensor 300 includes a two-dimensional array of pixels or cells each containing, in the example shown, a pair of capacitive sensor electrodes 301 and 302, formed by patterned conductive plates over a substrate containing devices (not shown) implementing the detection and control circuitry. An interlevel dielectric 304 (e.g., an oxide) is disposed over and between the capacitive sensor electrodes 301 and 302. A passivation layer 305 is disposed over the interlevel dielectric 304 and forms a sensor surface 306 on which the finger is placed for sensing of the fingerprint pattern.

A problem with capacitive fingerprint sensors of the type described is localized surface damage 307 (e.g., scallops or troughs) and other irregularities in the sensing surface 306 of the top passivation layer 305. At the levels of 10 to 40 microns ($\mu$m) in length and less than 1 $\mu$m wide, such surface irregularities are virtually impossible to detect with microscopic inspection. With such light damage, the fingerprint can still initially be detected by the affected pixels and the damage is not visible in the fingerprint image.

During use, however, the damage site degrades over time, modulating the pixel and changing the image. The pixel gain may degrade, for example, to approximately one third of the original gain, behaving as if coupled to a floating capacitive plate located in the region of the surface damage. The surface damage or irregularity thus manifests after roughly one to three months of use as a "white" region in the fingerprint image (i.e., a dead or largely insensitive region within the sensor array) resulting from an increase in the interference between coupling of the capacitor plates. Therefore, fingerprint sensor devices initially functioning properly become functionally unacceptable after only a relatively brief period of use, without knowledge of (or any means for detecting) the surface damage or irregularity because no method of screening the problem was known.

There is clearly a need in the art for a method of detecting minute levels of surface damage and/or irregularity above the sensor capacitors of a fingerprint sensor device or other coupled fringe capacitor circuit.

SUMMARY OF THE INVENTION

To address the above-discussed deficiencies of the prior art, it is a primary object of the present invention to provide, for use in integrated circuits, a technique for detecting minute surface damage and irregularities on the sensing surface of a capacitive integrated circuit by acquiring a preliminary image of the capacitance readings for the sensor array, coating the sensing surface with an electrolyte solution, then acquiring an additional image while the sensing surface is coated and/or after the electrolyte solution is removed. The electrolyte solution accelerates manifestation of pixel degradation and failure caused by surface damage or irregularities. Defective regions are identified by change of grayscale pixels in the preliminary image while the electrolyte coating is on the sensing surface and then again after the electrolyte coating is removed.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art will appreciate that they may readily use the conception and the specific embodiment disclosed as a basis for modifying or designing other structures for carrying out the same purposes of the present invention. Those skilled in the art will also realize that such equivalent constructions do not depart from the spirit and scope of the invention in its broadest form.

Before undertaking the DETAILED DESCRIPTION OF THE INVENTION below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION OF THE INVENTION

FIGS. 1A–1B through 2A–2D, discussed below, and the various embodiment used to describe the principles of the present invention in this patent document are by way of illustration only and should not be construed in any way to limit the scope of the invention. Those skilled in the art will understand that the principles of the present invention may be implemented in any suitably arranged device.

Figure 1A:
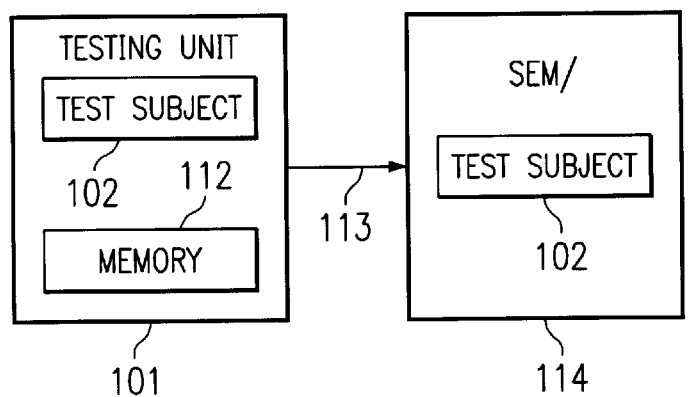
FIGS. 1A–1B depict detection of minute level surface damage or irregularity on the sensing surface of capacitive sensor integrated circuits according to one embodiment of the present invention.
Figure 1B:
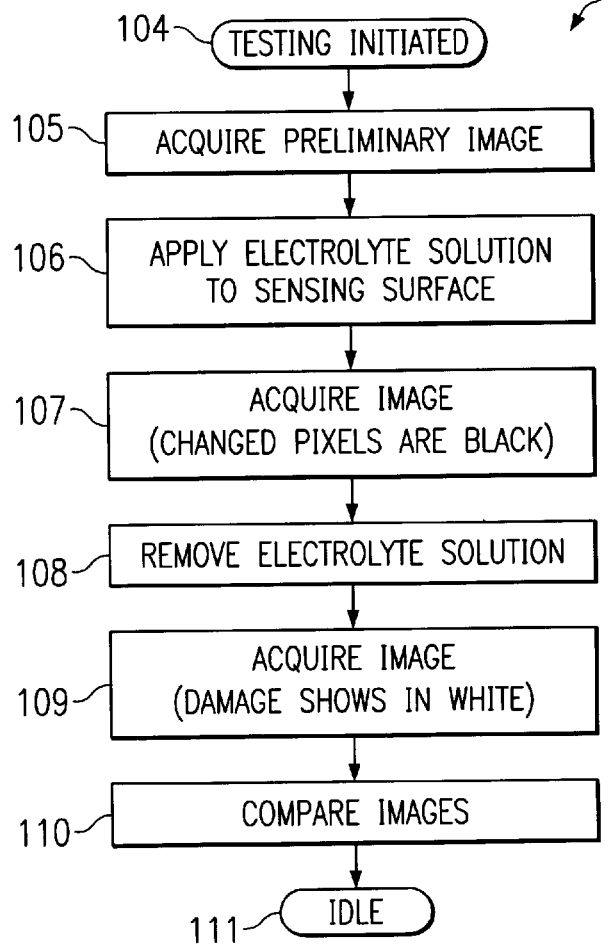

FIGS. 1A and 1B depict detection of minute level surface damage or irregularity on the sensing surface of capacitive sensor integrated circuits according to one embodiment of the present invention. FIG. 1A is a block diagram of a test system for detecting minute level surface damage on the sensing surface of capacitive integrated circuits. Test system 100 includes a test unit 101 performing the process described below on testing subject 102. Test subject 102 may be an individual capacitive integrated circuit, either before or after packaging, or a wafer containing a plurality of capacitive sensor integrated circuit dies. In either case, however, testing unit 101 connects to the detection and control circuitry within the capacitive integrated circuit test subject 102. Testing unit 101 also includes memory 112.

FIG. 1B is a high level flow chart for a process of detecting minute level surface damage or irregularity on the sensing surface of capacitive sensor integrated circuits according to one embodiment of the present invention. Process 103 begins with connection to the capacitive sensor array within the integrated circuit test subject 102 and initiation of testing (step 104). A preliminary image of the "grayscale" output of the capacitor sensor array (i.e., the output before the sensitivity of the array is enhanced or degraded) is then taken as a reference (step 105) by reading the capacitor values.

The sensing surface is then coated with an electrolyte solution to "decorate" the damaged regions or irregularities (step 106). A strong electrolyte solution such as sodium chloride (NaCl) is employed to accelerate changes to the capacitive array output which are normally seen only over time. The preferred electrolyte solution is one part saturated sodium chloride solution (in water) with two parts methanol. Other strong electrolytes such as potassium hydroxide (KaOH) solution or weak electrolytes such as citric acid or sodium bicarbonate solution may also be suitably employed.

Silicon-based passivation materials used to form the sensing surface tend to be hydrophobic, such that a simple electrolyte solution will not wet the surface well. While alcohol solutions exhibit better surface tension, sodium chloride does not dissolve well in alcohol. Accordingly, the preferred electrolyte solution is a combination of saturated saline and methanol as described above, since the methanol breaks down the surface tension and promotes adhesion. However, other surfactants or solvents having low surface tension may be employed in lieu of alcohol or methanol, or may not be necessary depending on the composition of the sensing surface.

Once the sensing surface of the capacitive sensor integrated circuit has been coated with the electrolyte solution, the values of the capacitor readings are again taken (step 107) and compared with the original image. The presence of the electrolyte solution increases the capacitive coupling of the conductive plates forming the sensor array and the sensitivity of the pixels, acting as a grounded plate over the sensor array. Within an image detection system in which the gain increases with capacitive coupling to a pair of conductive surfaces forming a pixel, any change to the functionality of the capacitive sensor array will appear with the affected pixels showing as black. In other image detection systems, however, the change may manifest in a different manner.

The electrolyte solution is then removed by a precision wipe (step 108), and the image is again taken by reading the pixel capacitance values (step 109). Pixels with surface damage or irregularities, which manifest as a localized floating plate or plates over the capacitive sensor conductive plates which collect charge, will now show in the image as white for an image detection system of the type described above. As noted, the change may manifest itself in a different manner when a different image detection mechanism is employed with the capacitive sensors.

The images with the electrolyte solution present and after removal of the electrolyte solution are thus compared to the preliminary image (step 110), either visually or algorithmically, and the areas indicated to have surface damage or irregularities are identified by the change(s) in the pixels of the image. These locations may then be utilized with a scanning electron microscope (SEM) or optical microscope to locate the damage identified by decoration with the electrolyte solution.

Capacitive sensor integrated circuits which are found to have surface damage or irregularities may be either discarded or modified to disable the pixels affected by the surface damage if such modification permits acceptable performance. The process then becomes idle (step 111) until another capacitive sensor integrated circuit is tested.

Referring back to FIG. 1A, testing unit 101 includes a memory 112 for storing the image data during testing, as well as conventional processing modules (not shown) for comparing the image data and identifying changes and/or controlling the operation of testing unit 101. Testing system 100 may also include a data link 113 to the microscope 114 which is utilized to examine the sensing surface damage identified.

Figure 2A:
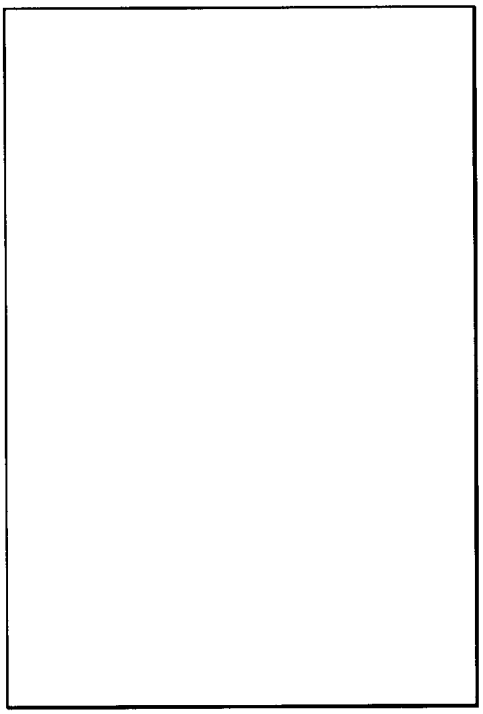
FIGS. 2A–2 illustrate capacitive sensor array images during detection of minute level surface damage or irregularity on the sensing surface according to one embodiment of the present invention.

FIGS. 2A through 2D illustrate capacitive sensor array images during detection of minute level surface damage or irregularities on the sensing surface according to one embodiment of the present invention. Each of the images was acquired with a single capacitive sensor integrated circuit. FIG. 2A illustrates an initial "grayscale" image of a capacitive sensor array prior to application of an electrolyte solution. No surface damage or irregularities are visible.

Figure 2B:
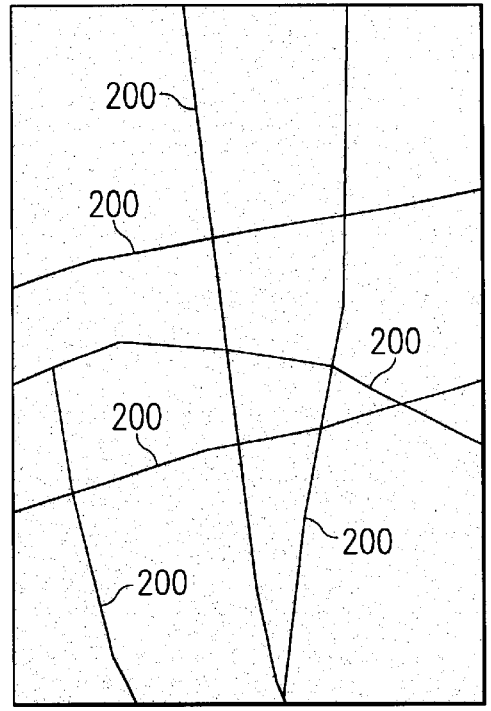

FIG. 2B illustrates the image acquired by the same sensor array while the electrolyte solution is present on the sensing surface of the capacitive sensor integrated circuit. Narrow surface scratches 200 appear as lines within the image, with the lines appearing generally darker than undamaged pixels because of the pixel gain mechanism employed.

Figure 2C:
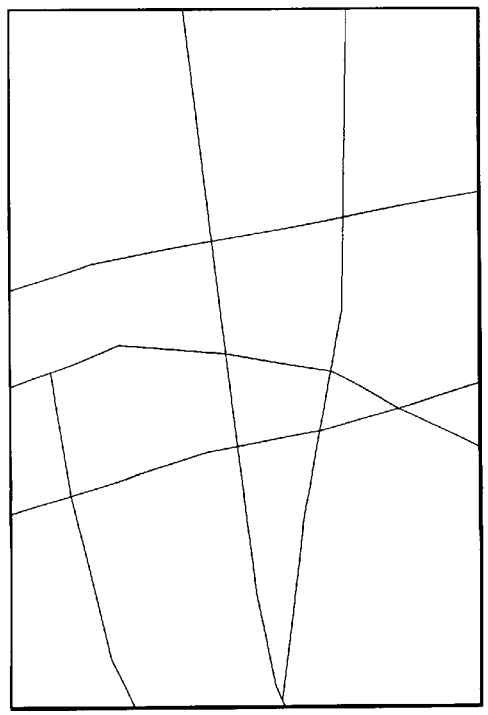
Figure 2D:
Figure 3A:
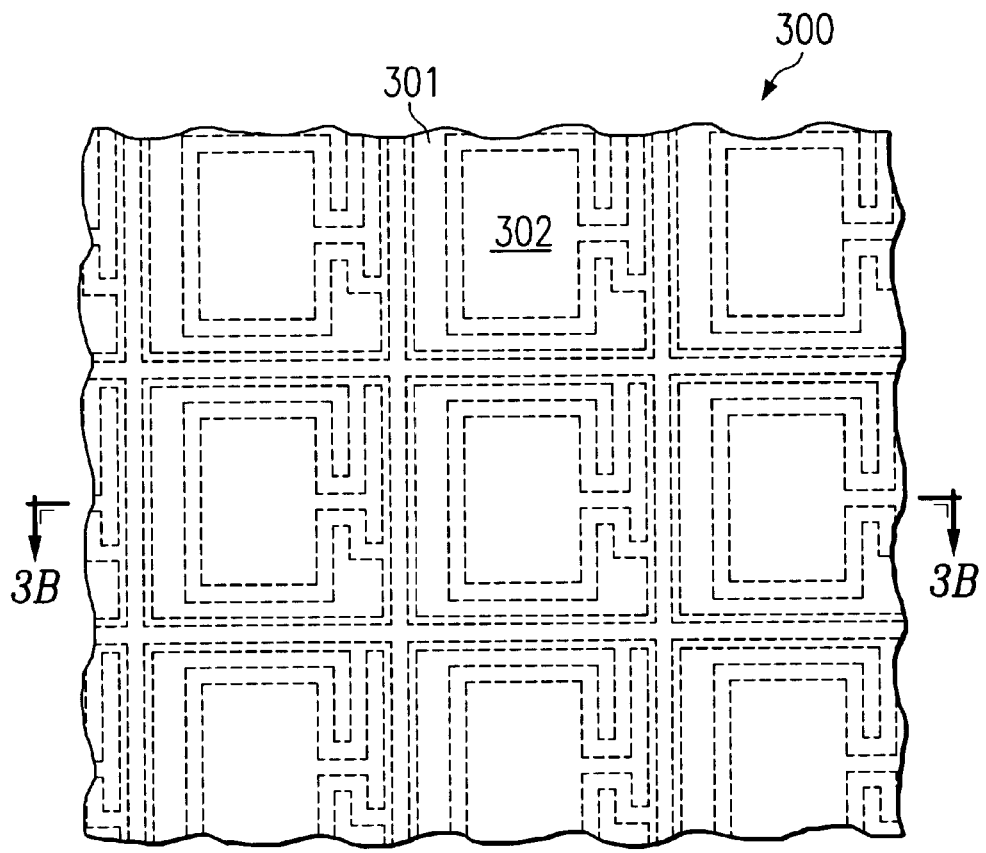
FIGS. 3A–3B are various views of a capacitive fingerprint sensor.
Figure 3B:
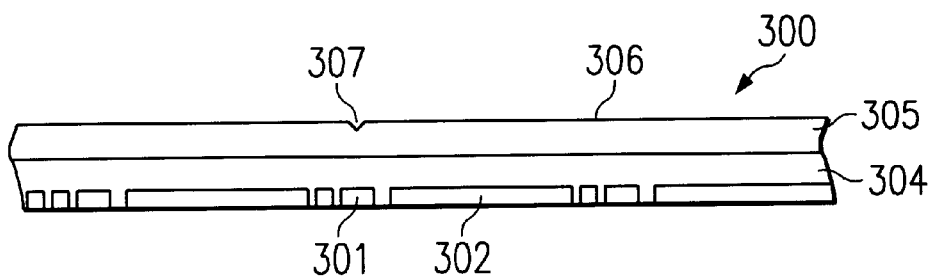

FIG. 2C illustrates the image of the sensor array after removal of the electrolyte solution, where at least some of the scratches remain apparent, but as white lines. FIG. 2D illustrates a fingerprint image acquired utilizing the capacitor integrated circuit sensor after the damage was decorated out with the electrolyte solution. The scratches are clearly evident, superimposed on the fingerprint features.

The present invention accelerates manifestation of the effect of extremely minute surface damage or irregularities on the sensing surface of a coupled-capacitance integrated circuit such as a fingerprint sensor. The damage or irregularities may be detected long prior to ordinary manifestation during use.

Although the present invention has been described in detail, those skilled in the art will understand that various changes, substitutions, variations, enhancements, nuances, gradations, lesser forms, alterations, revisions, improvements and knock-offs of the invention disclosed herein may be made without departing from the spirit and scope of the invention in its broadest form.

What is claimed is:

1. For use with capacitive sensor integrated circuits, a method of detecting surface damage comprising:
   acquiring a preliminary image for a plurality of capacitive sensors;
   coating a sensing surface for the capacitive sensors with an electrolyte solution;
   acquiring at least one additional image for the capacitive sensors either while the electrolyte solution is on the sensing surface or after the electrolyte solution is removed from the sensing surface; and
   comparing the preliminary image with the at least one additional image to detect defects on the sensing surface from pixel changes.

2. The method as set forth in claim 1 wherein the step of acquiring at least one additional image for the capacitive sensors either while the electrolyte solution is on the sensing surface or after the electrolyte solution is removed from the sensing surface further comprises:
   acquiring a first additional image while the electrolyte solution is on the sensing surface; and
   acquiring a second additional image after the electrolyte solution is removed from the sensing surface.

3. The method as set forth in claim 2 wherein the step of comparing the preliminary image with the at least one additional image to detect defects on the sensing surface from pixel changes further comprises:
   comparing the preliminary image with the first additional image; and
   comparing the preliminary image with the second additional image.

4. The method as set forth in claim 3 further comprising:
   detecting surface damage from a change of pixels from gray in the preliminary image to black in the first additional image and then to white in the second additional image.

5. The method as set forth in claim 1 wherein the step of coating a sensing surface for the capacitive sensors with an electrolyte solution further comprises:
   coating the sensing surface with a solution containing one part saturated saline and two parts methanol.

6. The method as set forth in claim 1 wherein the step of comparing the preliminary image with the at least one additional image to detect defects on the sensing surface from pixel changes further comprises:
   detecting damaged regions having a length not greater than about 10 to 40 microns and a width of less than 1 micron.

7. The method as set forth in claim 1 wherein the steps of acquiring at least one additional image for the capacitive sensors either while the electrolyte solution is on the sensing surface or after the electrolyte solution is removed from the sensing surface and comparing the preliminary image with the at least one additional image to detect defects on the sensing surface from pixel changes further comprise:
   acquiring an additional image for the capacitive sensors while the electrolyte solution is on the sensing surface; and
   detecting surface damage in the sensing surface over a set of pixels, each containing one of the capacitive sensors from gray in the preliminary image to black in the additional image.

8. The method as set forth in claim 1 wherein the steps of acquiring at least one additional image for the capacitive sensors either while the electrolyte solution is on the sensing surface or after the electrolyte solution is removed from the sensing surface and comparing the preliminary image with the at least one additional image to detect defects on the sensing surface from pixel changes further comprise:
   acquiring an additional image for the capacitive sensors after the electrolyte solution has been removed from the sensing surface; and
   detecting surface damage in the sensing surface over a set of pixels, each containing one of the capacitive sensors from gray in the preliminary image to white in the additional image.

9. The method as set forth in claim 1 wherein the steps of acquiring at least one additional image for the capacitive sensors either while the electrolyte solution is on the sensing surface or after the electrolyte solution is removed from the sensing surface and comparing the preliminary image with the at least one additional image to detect defects on the sensing surface from pixel changes further comprise:
   acquiring a first additional image for the capacitive sensors while the electrolyte solution is on the sensing surface;
   acquiring a second additional image for the capacitive sensors after the electrolyte solution has been removed from the sensing surface; and
   detecting surface damage in the sensing surface over a set of pixels, each containing one of the capacitive sensors from gray in the preliminary image to black in the first additional image and then to white in the second additional image.

10. For use with capacitive sensor integrated circuits, a mechanism for detecting surface damage comprising:
    means for acquiring a preliminary image for a plurality of capacitive sensors;
    means for coating a sensing surface for the capacitive sensors with an electrolyte solution;
    means for acquiring at least one additional image for the capacitive sensors either while the electrolyte solution is on the sensing surface or after the electrolyte solution is removed from the sensing surface; and
    means for comparing the preliminary image with the at least one additional image to detect defects on the sensing surface from pixel changes.

11. The mechanism as set forth in claim 10 wherein the means for acquiring at least one additional image for the capacitive sensors either while the electrolyte solution is on the sensing surface or after the electrolyte solution is removed from the sensing surface further comprises:
    means for acquiring a first additional image while the electrolyte solution is on the sensing surface; and
    means for acquiring a second additional image after the electrolyte solution is removed from the sensing surface.

12. The mechanism as set forth in claim 11 wherein the means for comparing the preliminary image with the at least one additional image to detect defects on the sensing surface from pixel changes further comprises:
    means for comparing the preliminary image with the first additional image; and
    means for comparing the preliminary image with the second additional image.

13. The mechanism as set forth in claim 12 further comprising:

means for detecting surface damage from a change of pixels from gray in the preliminary image to black in the first additional image and then to white in the second additional image.

14. The mechanism as set forth in claim 10 wherein the means for coating a sensing surface for the capacitive sensors with an electrolyte solution further comprises:

means for coating the sensing surface with a solution containing one part saturated saline and two parts methanol.

15. The mechanism as set forth in claim 10 wherein the means for comparing the preliminary image with the at least one additional image to detect defects on the sensing surface from pixel changes further comprises:

means for detecting damaged regions having a length not greater than about 10 to 40 microns and a width of less than 1 micron.

16. The mechanism as set forth in claim 10 wherein the means for acquiring at least one additional image for the capacitive sensors either while the electrolyte solution is on the sensing surface or after the electrolyte solution is removed from the sensing surface and the means for comparing the preliminary image with the at least one additional image to detect defects on the sensing surface from pixel changes further comprise:

means for acquiring an additional image for the capacitive sensors while the electrolyte solution is on the sensing surface; and means for detecting surface damage in the sensing surface over a set of pixels, each containing one of the capacitive sensors from gray in the preliminary image to black in the additional image.

17. The mechanism as set forth in claim 10 wherein the means for acquiring at least one additional image for the capacitive sensors either while the electrolyte solution is on the sensing surface or after the electrolyte solution is removed from the sensing surface and the means for comparing the preliminary image with the at least one additional image to detect defects on the sensing surface from pixel changes further comprise:

means for acquiring an additional image for the capacitive sensors after the electrolyte solution has been removed from the sensing surface; and means for detecting surface damage in the sensing surface over a set of pixels, each containing one of the capacitive sensors from gray in the preliminary image to white in the additional image.

18. The mechanism as set forth in claim 10 wherein the means for acquiring at least one additional image for the capacitive sensors either while the electrolyte solution is on the sensing surface or after the electrolyte solution is removed from the sensing surface and the means for comparing the preliminary image with the at least one additional image to detect defects on the sensing surface from pixel changes further comprise:

means for acquiring a first additional image for the capacitive sensors while the electrolyte solution is on the sensing surface;

means for acquiring a second additional image for the capacitive sensors after the electrolyte solution has been removed from the sensing surface; and means for detecting surface damage in the sensing surface over a set of pixels each containing one of the capacitive plate sensors from gray in the preliminary image to black in the first additional image and then to white in the second additional image.

19. For use with capacitive sensor integrated circuits, a method of detecting surface damage comprising:

acquiring a preliminary image of capacitance readings for a two-dimensional array of capacitive sensors;

coating a sensing surface for the capacitive sensors with an electrolyte solution containing one part saturated saline solution and two parts methanol;

acquiring a first additional image of capacitance readings for the capacitive sensors while the electrolyte solution is on the sensing surface;

removing the electrolyte solution from the sensing surface;

acquiring a second additional image of capacitance readings for the capacitive sensors after the electrolyte solution is removed from the sensing surface; and comparing the first and second additional images to the preliminary image to detect surface damage on the sensing surface from changes in pixels each containing one of the capacitive sensors from the preliminary image to the first additional image and from the first additional image to the second additional image.

20. The method as set forth in claim 19 further comprising:

detecting surface damage regions on the sensing surface having a length not greater than about 10 to 40 microns and a width of less than 1 micron.

* * * * *